United States Patent
Bortinger et al.

(10) Patent No.: US 6,858,561 B2
(45) Date of Patent: Feb. 22, 2005

(54) PHOSPHORUS/VANADIUM CATALYST PREPARATION

(75) Inventors: Arie Bortinger, Ridgewood, NJ (US); Gianluca Mazzoni, Torre Boldone (IT); Tiziana Monti, Borgo Tossignano (IT)

(73) Assignees: Scientific Design Company, Inc., Little Ferry, NJ (US); Lonza S.p.A., Bergano (IT)

( * ) Notice: Subject to any disclaimer, the term of this patent is extended or adjusted under 35 U.S.C. 154(b) by 21 days.

(21) Appl. No.: 10/438,425

(22) Filed: May 15, 2003

(65) Prior Publication Data

US 2004/0229750 A1 Nov. 18, 2004

(51) Int. Cl.[7] ............... B01J 27/198; B01J 27/14; B01J 27/188; B01J 27/19; B01J 27/192
(52) U.S. Cl. .............. 502/209; 502/208; 502/210; 502/211; 502/212; 502/213; 502/214
(58) Field of Search ............... 502/208–214

(56) References Cited

U.S. PATENT DOCUMENTS

| | | | |
|---|---|---|---|
| 3,975,300 A | 8/1976 | Burress | 252/435 |
| 4,064,070 A | 12/1977 | Harrison | 252/435 |
| 4,132,670 A | 1/1979 | Katsumoto et al. | 242/437 |
| 4,435,521 A * | 3/1984 | Yang et al. | 502/209 |
| 4,517,371 A | 5/1985 | Yang et al. | 549/239 |
| 4,569,925 A * | 2/1986 | Yang et al. | 502/209 |
| 4,996,179 A * | 2/1991 | Haddad et al. | 502/209 |
| 5,137,860 A | 8/1992 | Ebner et al. | 502/209 |
| 5,155,235 A | 10/1992 | Takashi et al. | 549/262 |
| 5,364,824 A | 11/1994 | Andrews et al. | 502/209 |
| 5,543,532 A * | 8/1996 | Kourtakis et al. | 549/260 |
| 5,885,919 A | 3/1999 | Bortinger | 502/209 |
| 5,922,637 A | 7/1999 | Bortinger | 502/209 |
| 6,107,234 A * | 8/2000 | Bortinger | 502/209 |
| 6,174,833 B1 | 1/2001 | Bertola et al. | 502/209 |
| 2004/0014990 A1 * | 1/2004 | Storck et al. | 549/259 |

OTHER PUBLICATIONS

Tabita et al Applied Catalysis A: vol. 103, pp. 281–290 (1993) No month.

* cited by examiner

Primary Examiner—Mark L. Bell
Assistant Examiner—Patricia L. Hailey
(74) Attorney, Agent, or Firm—William C. Long; Roberts & Roberts, LLP

(57) ABSTRACT

A process for preparing a catalyst for maleic anhydride production wherein a +5 vanadium compound such as $V_2O_5$, an anhydrous phosphoric acid, and optionally promoters are admixed in an organic alcohol solvent, the admixture is rapidly brought to reflux and thereafter refluxed to reduced the vanadium compound to the desired degree, the reflux mixture is cooled, precursor crystals are separated by filtration and then dried and calcined.

11 Claims, No Drawings

PHOSPHORUS/VANADIUM CATALYST PREPARATION

BACKGROUND OF THE INVENTION

1. Field of the Invention

The present invention relates to an improved method for the production of vanadium/phosphorus mixed oxide catalysts which have special utility for the production of maleic anhydride.

2. Description of the Prior Art

A great deal of work has been done in the preparation and use of vanadium phosphorus oxide catalysts for the production of maleic anhydride. See U.S. Pat. Nos. 5,137,860 and 5,364,824 for a comprehensive description of the efforts of prior workers in this area.

Efforts have been made to develop catalyst preparation procedures which do not involve the use of corrosive and hazardous reagents such as HCl and oxalic acid.

U.S. Pat. No. 4,517,371 for example, at column 4, lines 48–64 summarizes prior work as follows:

"Generalizing from the above discussion, conventional preoperative methods, including both the aqueous and organic solution techniques, are unsatisfactory in that:

(1) they usually require that the catalyst manufacturing equipment be fabricated of special corrosion-resistant materials of construction;

(2) they are troubled by serious waste-disposal problems arising out of the employment of hydrogen chloride, nitric acid or oxalic acid for the dissolution of the vanadium component;

(3) they generally require extended and complex procedures for activation of the precursor catalyst;

(4) the preparation of the precursor catalyst is generally complicated and inherently costly; and (5) the aqueous-based preparations result in catalysts of relatively poor activity and yield for converting butane to maleic anhydride."

The process provided by U.S. Pat. No. 4,517,371 is described at column 5, lines 18–43 as follows:

"In one aspect of the present invention there is provided a process for preparing a composition comprising vanadium, phosphorus and oxygen capable of catalyzing the oxidation of hydrocarbons comprising:

1. reacting a vanadium containing compound and a phosphorus containing compound in the presence of a liquid organic media in a manner and under conditions sufficient to form in said liquid organic media a heterogeneous, vanadium-phosphorus-oxygen first catalyst precursor composition having an atomic ratio of phosphorus to vanadium of from about 0.5:1 to about 2:1, and an average vanadium valence of from about 3.9 to about 4.7;

2. separating said first catalyst precursor composition with from said liquid organic media;

3. contacting said first catalyst precursor composition with at least one part by weight water per part by weight first catalyst precursor composition at a temperature of at least 30° C. to form a second vanadium-phosphorus-oxygen catalyst precursor composition;

4. separating said second catalyst precursor composition from said water; and 5. activating said second catalyst precursor composition."

Takita et al in an article entitled "Incorporation of promoter elements into the crystal lattice of $(VO)_2P_2O_7$ and its promotion effects on the oxidation of n-butane to maleic anhydride", Applied Catalysis A: General, Vol 103, pages 281–290 (1993) describe preparing a homogeneous solution of reduced and dissolved $V_2O_5$ in isobutanol was added $V_2O_5$ to isobutanol and refluxing for 10 hours, then adding 99% $H_3PO_4$. A solution of metal acetoacetonates in isobutanol was added and reflux continued for 1 hour. A small amount of water was added and a precipitate was formed and separated.

Our earlier U.S. Pat. No. 5,922,637 describes digesting a vanadium+5 compound in an organic solvent with added phosphorus compound at anhydrous conditions and later adding water and further digesting the material to obtain the catalyst precursor.

Our earlier U.S. Pat. No. 5,885,919 employs an additive such as dimethyl sulfoxide to produce an improved catalyst.

U.S. Pat. No. 3,975,300 employs a one-step procedure for the catalyst preparation in the absence of hydrogen halide by forming a paste of a vanadium compound, an organic reducing agent such as a glycol and a phosphorous compound and drying and calcining the paste.

U.S. Pat. Nos. 4,064,070, 4,132,670 and 6,174,833 discuss the use of a mixture of IBA/benzyl alcohol for the reduction of the V2O5. In all these cases there is a pre-reduction step of the vanadium pentoxide before the addition of phosphoric acid. This pre-reduction step is a separate reflux step of 3–5 hours. The $2^{nd}$ reflux starts after the addition of the phosphoric acid and takes between 3–20 hours. In this step the formation of the VPO precursor takes place. In the present invention there is a single reflux step without the need of a pre-reduction step.

U.S. Pat. No. 5,155,235 the synthesis is anhydrous with no chloride in which the $V_2O_5$ is first reduced in a solvent containing 60% IBA and 40% benzyl alcohol (2 hr reflux). Thereafter the reaction mixture is cooled and the promote acetylacetonat magnesium or Zr is added followed by the addition reflux. The product recovery is by filtration of the cool solution (note catalyst calcination is at 500° C./3 hr under nitrogen).

U.S. Pat. No. 5,137,860 this patent provides an example of chloride free synthesis in which the $V_2O_5$ was reduced by oxalic acid in IBA. The main focus of the patent is on catalyst activation to form an activated phase with air/nitrogen/steam.

According to this patent, the synthesis procedure consists of a reflux step of a reaction mixture containing $V_2O_5$ in IBA, oxalic acid and phosphoric acid. After 16 hours of reflux, 25% of the IBA present is stripped followed by decantation of the remainder of the IBA and drying of the residual slurry.

U.S. Pat No. 5,364,824 is similar to U.S. Pat. No. 5,137,860 but it also shows the use of Bi as a promoter in a synthesis also with oxalic acid and IBA. The promoter was added after an overnight reflux step with phosphoric acid and cool down followed by another reflux step. This was referred as RCR (reflux cool down reflux).

The present invention provides a still further improved process for the preparation of VPO catalysts having special utility in the oxidation of $C_4$ hydrocarbons to form maleic anhydride.

BRIEF SUMMARY OF THE INVENTION

In particular the catalyst is prepared according to the invention by forming an admixture of a +5 vanadium compound such as $V_2O_5$, organic solvent such as isobutanol and/or benzyl alcohol and a phosphorus compound such as 100% phosphoric acid. Promoters such as bismuth, molybdenum or lithium compounds can also be added; mixtures of promoters can be used.

The mixture is then brought to reflux fairly rapidly, i.e. in less than 3 hours and probably in less than 2 hours. The reflux is continued to complete the reduction of the vanadium compound, i.e. 0.5 to 24 hours, preferably 3 to 12 hours.

DETAILED DESCRIPTION

The various materials used in the preparation of the catalyst are generally known. Thus, although $V_2O_5$ is the preferred vanadium starting material, various other vanadium compounds can be employed as is known in the art.

Similarly, phosphorous compounds employed to provide the phosphorous component are known. Especially preferred are the anhydrous phosphoric acid compounds such as orthophosphoric acid, polyphosphoric acid which is available as a mixture of orthophosphoric acid with pyrophosphoric acid, triphosphoric and higher acids and is sold on the basis of its calculated content of $H_3PO_4$, as for example 115%. Superphosphoric acid is a similar mixture sold as 105% $H_3PO_4$. The phosphorus component is employed in amount to provide a P:V atomic ratio of 1.0–1.8/1.

The organic liquid media used is likewise of a known type and functions as a suspending agent for the vanadium compound, as a solvent and/or diluent for the phosphorous compound, as a reducing agent for the vanadium compound and as a suspending agent for the formed catalyst precursor. A comprehensive listing is provided in U.S. Pat. No. 4,517,371, preferred in practice of this invention is the combination of isobutanol and benzyl alcohol, the benzyl alcohol preferably comprising at least 5 vol % and less that 30 vol % of the combination.

Promoters of the type and in amounts known in this art can be employed. The relative amounts of vanadium compound, phosphorous compound and promoters employed are well known in the art.

In the preparation sequence of the invention, the solid, vanadium compound, e.g. $V_2O_5$, and the phosphorus compound to anhydrous organic solvent media along with such promoters as are used and are added the mixture is rapidly heated to reflux and digested at reflux conditions for 0.5 to 24 hours under anhydrous conditions. During this anhydrous digestion period, the vanadium compound is maintained in the solid phase and undergoes reduction to a vanadium valence of about 3.9 to about 4.4. Preferably, the digestion is carried out by refluxing the mixture at essentially atmospheric conditions for the desired time. During the digestion at reflux conditions, such water as is formed is removed as by use of a Dean Stark separator in order to maintain anhydrous conditions.

The amount of organic solvent which is employed is less than 15 ml solvent per gram of added $V_2O_5$ in order than the vanadium component be maintained primarily in the solid phase throughout the digestion.

As described in U.S. Pat. No. 6,107,234, the catalyst precursor is conveniently represented by the (VO) $HPO_4 aH_2OM_m P_p O_y$ wherein M is at least one promoter element selected from the group consisting of elements from Groups IA, IB, IIA, IIIB, IVA, IVB, VA, VB, VIA, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present. Although the VPO precursor has been identified as $VOHPO_4 \cdot 0.5H_2O$, it is unclear as to the exact structure of the metal promoters in the presence of the excess phosphorus and therefore the above representation is a useful one.

After completion of the digestion, it is useful to concentrate the solid catalyst precursor by stripping off solvent and then recovering the precursor solid by filtration. The recovered solid is advantageously washed with organic solvent, e.g. isobutanol, and the final removal of organics from the precursor is carried out in a drying step in an oven at a temperature in the range of 100 to 180° C. for 1–24 hours. Lower temperatures and longer times can be used. Reduced pressure can also be applied to lower oven temperatures. Following drying, calcination of the dried catalyst precursor is carried out at a temperature in the range of about 200 to 300° for a sufficient period to improve the catalytic properties of the composition and remove volatile materials, usually 1–15 hours.

Following calcination, the catalyst precursor is activated by known procedures such as those shown in U.S. Pat. No. 6,107,234. This activation takes place at 350–550° C., for about 1–10 hours and results in the formation of catalyst which can then be used in the production of maleic anhydride. Where the catalyst is ultimately to be used in the form of pellets in a fixed bed reactor, the catalyst precursor after drying and calcining can be formed into the final pellets and then activated or the precursor after drying and calcining can first be activated and then formed into pellets.

In activation, the catalyst precursor is first heated at temperatures not exceeding 300° C. under an atmosphere which can be air, steam, inert gas, or a mixture for a time generally of 1–24 hours.

Following this, an atmosphere containing molecular oxygen, steam and optionally an inert gas is provided as above indicated and the temperature is increased at a rate of about 0.5° C. to 15° C. per minute to a value effective to eliminate water of hydration from the catalyst precursor, e.g. 350° C. to 550° C., preferably 400° C. to 450° C.

The precursor is maintained at the adjusted temperature under an oxygen and steam containing atmosphere to complete vanadium conversion to an oxidation state of about +4.0 to about +4.5 and for the transformation of the precursor to the active catalyst which has the formula $(VO)_2P_2O_7 M_{2m} P_{2p} O_y$ wherein M, m, p and y are as defined about. It is essential in this step that the atmosphere contain at least 1 vol % oxygen up to about 15 vol % oxygen, preferably at least 2 vol % oxygen and desirably 3–8 vol % oxygen. It is important to minimize the exotherm during this process.

The following examples illustrate the invention.

EXAMPLE 1

Into a 12 liter round flask equipped with a mechanical stirrer, a gas inlet tube, a thermowell, a condenser and a heating mantle were charged 7260 ml anhydrous isobutanol, 806 ml benzyl alcohol, 66.896 g of bismuth solution containing 28 wt % Bi (as a bismuth salt of 2-ethylhexanoic acid in mineral spirits supplied by the OMG company and sold as Catalyst code 320), 815.1 grams $V_2O_5$. About 1207.8 g of 100% phosphoric acid were added slowly into the reaction mixture while stirring.

The reaction mixture was brought to reflux within 90 minutes and the reflux was continued overnight. Thereafter the reaction mixture was cooled down and filtered by vacuum filtration. The product cake was then dried in an oven at 110° C. for 10 hours and finally at 150° C. for 16 hours. The dry cake was crushed and calcined at 220° C. for 3 hours and then at 260° C. for another 3 hours. The calcined powder was mixed with 4% graphite and was formed into 3/16"×3/16" tablets with a 1/16" I.D center hole. The catalyst in the pellet form was activated in an oven by procedures described in U.S. Pat. No. 6,107,234. with 4.5% oxygen/50% steam/nitrogen balance at about 425° C. for 6 hours. The oven was cooled down and steam was removed when the bed temperature reached about 250° Thereafter the catalyst bed was cooled down to room temperature under dry gas containing 9% oxygen/nitrogen balance by volume.

The performance test was done in a 5 foot stainless steel reactor tube, 1 inch O.D. packed with a 3.5 feet catalyst bed. Butane at a controlled concentration in air was used as feed for catalyst evaluation. The catalytic activity is shown in Table 1, Example 1.

EXAMPLE 2

This example illustrates the effect of a two fold increase of the concentration of benzyl alcohol in the total alcohol mixture used in the synthesis. The synthesis of Example 1 was generally repeated except that the amount of benzyl alcohol was increased to 1613 ml while maintaining the same volume of the total alcohols used. The performance of this catalyst is shown in Table 1, Example 2.

EXAMPLE 3—COMPARATIVE EXAMPLE 1

This example illustrates the effect of a pre-reduction step prior to the addition of the phosphoric acid.

The synthesis of Example 1 was generally repeated except that the all the reagents were added except the phosphoric acid and the reaction mixture was brought to reflux. The reflux was continued for 4 hours in order to reduce the $V_2O_5$. Thereafter, the phosphoric acid was added slowly into the reaction slurry and the reflux was continued overnight. The remaining steps are as described in Example 1. The performance of this catalyst is shown in Table 1, Example 3.

EXAMPLE 4

This example illustrates the effect of the addition of a molybdenum promoter.

The synthesis of Example 1 was generally repeated except that a molybdenum promoter was provided by adding at room temperature 43.0 gram of molybdenum Hex-Cem (this material is a molybdenum salt of 2-ethylhexanoic acid and contains 15% wt molybdenum. The material was obtained from the OMG Company, Catalyst code 00962) before reflux. The performance of this catalyst is shown in Table 1, Example 4.

EXAMPLE 5

The synthesis of Example 4 was repeated except the source of the molybdenum precursor was phosphomolybdic acid while maintaining the same atomic ratio of Mo/V to 0.0075. The catalytic activity is shown in Table 2, Example 5.

EXAMPLE 6

The effect of Li as a promoter was examined in this example.

The synthesis of example 1 was generally repeated except that 9.14 grams of lithium acetate dehydrate was also added into the reaction mixture before reflux. The catalytic activity is shown in Table 2, Example 6.

EXAMPLE 7—COMPARATIVE EXAMPLE 2

The purpose of the comparative example is to compare the wet end synthesis step.

The procedure of Example 12 of U.S. Pat. No. 5,506,187 was repeated except that the catalyst shape was as in Example 1. The catalytic activity is shown in Table 2, Example 7.

EXAMPLE 8—COMPARATIVE EXAMPLE 3

The purpose of the comparative example is to compare the wet end synthesis step in a synthesis using DMSO.

The synthesis of Example 1 was repeated except for the following changes. About 70 grams of DMSO (dimethyl sulfoxide) were added with the alcohol at room temperature before the addition of the phosphoric acid. After overnight reflux, the reaction mixture was cooled down to room temperature and 80 ml of 30% hydrogen peroxide were added while stirring. After 30 minutes of stirring, the reaction mixture was filtered and the remaining procedures of Example 1 were followed. The catalytic activity is shown in Table 2, Example 8. As a result of the hydrogen peroxide addition, the sulfur compound odor, normally associated with the product was eliminated.

EXAMPLE 9

The effect of using 97% phosphoric acid instead of 100% phosphoric acid was examined in this example contributing to a less anhydrous condition in the initial reaction mixture.

The synthesis of Example 1 was generally repeated except that 97% phosphoric acid was used while maintaining the same ratio of P/V in the reaction mixture. The catalytic activity is shown in Table 3, Example 9.

EXAMPLE 10

The effect of using less anhydrous conditions in the initial reaction mixture was evaluated by adding 2 wt % water based on the total alcohol used in the reaction mixture.

The synthesis of Example 1 was generally repeated except that 133 grams of deionized water was added at room temperature before the 100% phosphoric acid was added. The catalytic activity is shown in Table 3, Example 10.

TABLE 1[1]

| Example | 2 | 3 | 4 |
|---|---|---|---|
| Hours | 460 | 355 | 403 | 417 |
| Salt ° C. | 368 | 378 | 369 | 364 |
| % Conversion | 79.5 | 80.5 | 81.1 | 79.4 |
| % Selectivity | 72.3 | 67.7 | 66.6 | 67.7 |
| Wt % Yield | 97.0 | 92.1 | 91.3 | 90.8 |

[1]1" OD × 5' Reactor; 3.5' bed without a thermowell; the pellets tested were 3/16" × 3/16" with 1/16" hole in the center: The space velocity in Examples 1–4 was 2250 h$^{-1}$, feed was about 1.25% butane.

TABLE 2[1]

| Example | 5 | 6 | 7[2] | 8[2] |
|---|---|---|---|---|
| Hours | 332 | 408 | 378 | 451 |
| Salt ° C. | 375 | 378 | 408 | 384 |
| % Conversion | 80.8 | 79.7 | 80.7 | 80.1 |
| % Selectivity | 66.4 | 69.9 | 62.0 | 70.4 |
| Wt % Yield | 90.8 | 94.3 | 84.7 | 95.5 |

TABLE 2[1]-continued

| Example | 5 | 6 | 7[2] | 8[2] |
|---|---|---|---|---|

[1]1" OD × 5' Reactor; 3.5' bed without a thermowell; the pellets tested were 3/16" × 3/16" with 1/16" hole in the center. The space velocity in Examples 5–7 was 2250 h$^{-1}$, and in Example 8 it was 2500 h$^{-1}$. The feed in Example 5–7 was about 1.25% butane and 1.30% butane in Example 8.
[2]1" OD × 5' Reactor; 3.5' bed with a thermowell, the bath temperature was increased by 3° C. to 371° C. to maintain about 80% conversion without significant changes in selectivity or yield.

TABLE 3[1]

| Example | 9 | 10 |
|---|---|---|
| Hours | 423 | 473 |
| Salt ° C. | 385 | 383 |
| % Conversion | 79.8 | 79.4 |
| % Selectivity | 71.4 | 69.9 |
| Wt % Yield | 96.3 | 93.8 |

[2]1" OD × 5' Reactor, 3.5' bed without a thermowell; the pellets tested were 3/16" × 3/16" with 1/16" hole in the center. The space velocity was 2250 h$^{-1}$, feed was about 1.25% butane.

The above examples illustrate that the present synthesis method clearly shows an advantage over the method which requires a pre-reduction step as shown by comparing Examples 1 and 3 (Comparative Example 1). A lower selectivity and yield was observed for the catalyst with the pre-reduction step although both catalysts show similar activity as indicated by about the same salt bath temperature at the same test conditions.

The catalyst in Example 1 also shows higher performance than the catalyst prepared by the procedure in Example 7 (Comparative Example 2). The catalyst in Example 1 shows higher yield, selectivity and activity as indicated by the significant lower temperature 368° C. vs 408° C.

Although the catalyst in Example 8 (Comparative Example 3) shows good performance, the current catalyst procedure illustrated in Example 1 shows an advantage by the eliminating the need to use hydrogen peroxide to eliminate the odorous materials formed during the synthesis with DMSO.

Furthermore, by elimination of a distillation step prior to filtration, an alcohol rinsing step is also avoided. Therefore, the current method is a further simplification of the synthesis method which will increase the cost benefits in commercial production.

The catalyst in Example 9 shows that good yield and selectivity can be obtained when using conditions in the reaction mixture are less anhydrous such as occurs when using 97% phosphoric acid compared with 100% phosphoric acid in Example 1. However, the catalyst shows lower activity as indicated by the more than 15° C. higher salt bath temperature required to obtain about 80% conversion. The catalyst in Example 10 prepared at a less anhydrous condition with 2 wt % water based on the total alcohol weight also shows lower activity as indicated by the higher salt bath temperature. The yield was also slightly lower. Therefore, anhydrous conditions are preferred in order to produce a catalyst with both high yield and activity.

We claim:
1. The method of preparing a vanadium phosphorus mixed oxide catalyst which comprises forming an admixture of a +5 vanadium compound and an anhydrous phosphoric acid in an organic alcohol solvent, said admixture optionally also comprised of promoter compounds, heating the admixture to reflux in less than 3 hours, refluxing the admixture for 0.5–24 hours, cooling the resulting refluxed admixture without removal of solvent by distillation, recovering catalyst precursor particles having the formula (VO)HPO$_4$aH$_2$OM$_m$P$_p$O$_y$ wherein M is at least one promoter element selected from the group consisting of elements form Group IA, IB, IIA, IIB, IIIA, IIIB, IVA, IVB, VA, VB, VIA, VIB, and VIIIA of the Periodic Table of Elements, and mixtures thereof, a is a number of at least about 0.3, m is a number of from about 0 to about 0.3, and y corresponds to the amount of oxygen necessary to satisfy the valence requirements of all elements present from the cooled admixture by filtration, drying and calcining the recovered particles without solvent washing for use as catalyst.
2. The method of claim 1 wherein said +5 vanadium compound is V$_2$O$_5$.
3. The method of claim 1 wherein said organic alcohol benzyl alcohol.
4. The method of claim 1 wherein said organic alcohol solvent comprises by volume isobutanol with up to 15% benzyl alcohol.
5. The method of claim 1 wherein said admixture comprises a bismuth promoter.
6. The method of claim 1 wherein said admixture comprises a molybdenum promoter.
7. The method of claim 1 wherein said admixture comprises a zinc promoter.
8. The method of claim 1 wherein said admixture comprises an alkali metal promoter.
9. The method of claim 1 wherein the recovered catalyst precursor particles are dried at 100–180° C. for 1–24 hours.
10. The method of claim 1 wherein the dried catalyst precursor is calcined at 200–300° C. for 1–15 hours.
11. The method of claim 1 wherein the catalyst precursor is activated by heating the catalyst precursor in an atmosphere selected from the group consisting of air, steam, inert gas, and mixtures thereof to a temperature not to exceed about 300° C., maintaining the catalyst precursor at this temperature and providing an atmosphere containing molecular oxygen, steam, and optionally an inert gas, increasing the temperature at a rate of rom about 0.5° C./min to about 15° C./min to a value effective to eliminate the water of hydration from the catalyst precursor, adjusting the temperature in a molecular oxygen/steam containing atmosphere comprised of at least 1 vol % oxygen for a time effective to provide a vanadium oxidation state of from about +4.0 to about +4.5 to complete transformation to the active catalyst having the formula (VO)$_2$P$_2$O$_7$M$_{2m}$P$_{2p}$O$_y$ wherein M, m, p and y are as defined in claim 1.

* * * * *